United States Patent [19]
Bagaoisan et al.

[11] Patent Number: 6,152,909
[45] Date of Patent: Nov. 28, 2000

[54] ASPIRATION SYSTEM AND METHOD

[75] Inventors: Celso J. Bagaoisan, Union City; Hung V. Ha, San Jose; Mukund R. Patel, San Jose; Sivette Lam, San Jose; Mir Imran, Los Altos Hills, all of Calif.

[73] Assignee: Percusurge, Inc., Sunnyvale, Calif.

[21] Appl. No.: 09/026,013

[22] Filed: Feb. 19, 1998

Related U.S. Application Data

[63] Continuation-in-part of application No. 08/813,808, Mar. 6, 1997, abandoned, and a continuation-in-part of application No. 08/813,807, Mar. 6, 1997, abandoned, and a continuation-in-part of application No. 08/812,875, Mar. 6, 1997, Pat. No. 5,833,644, which is a continuation-in-part of application No. 08/650,464, May 20, 1996, abandoned.

[51] Int. Cl.$^7$ .................................................. A61M 25/00
[52] U.S. Cl. ........................... 604/523; 604/173; 604/264
[58] Field of Search ................................ 604/523, 27, 30, 604/32, 33, 35, 36, 48, 93, 173, 181, 246, 248, 249, 264, 524, 535, 537, 199, 93.01

[56] References Cited

U.S. PATENT DOCUMENTS

| | | |
|---|---|---|
| 3,144,868 | 8/1964 | Jascalevich . |
| 4,468,216 | 8/1984 | Muto . |
| 4,511,354 | 4/1985 | Sterling . |
| 4,573,966 | 3/1986 | Weikl et al. . |
| 4,589,412 | 5/1986 | Kensey . |
| 4,610,662 | 9/1986 | Weikl et al. . |
| 4,662,871 | 5/1987 | Rafelson . |
| 4,692,139 | 9/1987 | Stiles . |
| 4,696,668 | 9/1987 | Wilcox . |
| 4,713,060 | 12/1987 | Riuli ........................................ 604/199 |
| 4,748,982 | 6/1988 | Horzewski et al. . |
| 4,754,755 | 7/1988 | Husted . |
| 4,782,834 | 11/1988 | Maguire et al. . |
| 4,784,636 | 11/1988 | Rydell . |
| 4,790,812 | 12/1988 | Hawkins, Jr., et al. . |
| 4,790,813 | 12/1988 | Kensey . |
| 4,850,957 | 7/1989 | Summers . |
| 4,867,156 | 9/1989 | Stack et al. . |

(List continued on next page.)

FOREIGN PATENT DOCUMENTS

| | | |
|---|---|---|
| 0693295A1 | 1/1996 | European Pat. Off. . |
| WO 95/15780 | 6/1995 | WIPO . |
| 96/15824 | 5/1996 | WIPO . |
| WO 97/44082 | 11/1997 | WIPO . |
| WO 98/44982 | 10/1998 | WIPO . |

OTHER PUBLICATIONS

"New Triple Coaxian Catheter System for Carotid Angioplasty with Cerebral Protection" Theron, et al., AJNR 11:869–874 Sep./Oct. 1990.

Angiojet LF 140 Rapid Thrombectomy Catheter Brochure, Possis Medical, Inc., Publication No. 102301–001–02, Sep. 1995.

Angiojet F105 Rapid Thrombectomy Catheter Brochure, Possis Medical, Inc. Publication No. 102302–001–02, Sep. 1995.

*Primary Examiner*—Wynn Wood Coggins
*Assistant Examiner*—Cris L. Rodriguez
*Attorney, Agent, or Firm*—Knobbe, Martens, Olson & Bear, LLP

[57] ABSTRACT

Aspiration catheters and methods for the treatment of an occlusion in a blood vessel. These catheters and methods are especially useful in the removal of occlusions from saphenous vein grafts, the coronary and carotid arteries, arteries above the aortic arch and even smaller vessels. The catheters of the present invention are provided in either over-the-wire or in single operator form. Radiopaque markers are preferably incorporated into distal ends of the catheters, and visual markers are incorporated into the proximal end of the catheters, to facilitate their positioning within the body. The catheters are provided with varying flexibility along the length of the shaft, such that they are soft and flexible enough to be navigated through the vasculature of a patient without causing damage, but are stiff enough to sustain the axial push required to position the catheter properly and to sustain the aspiration pressures. Support mandrels and support sheaths may also be added to impart additional strength to the length of the catheter.

2 Claims, 10 Drawing Sheets

U.S. PATENT DOCUMENTS

| | | |
|---|---|---|
| 4,950,238 | 8/1990 | Sullivan . |
| 4,964,409 | 10/1990 | Tremulis . |
| 4,994,067 | 2/1991 | Summers . |
| 5,002,528 | 3/1991 | Palestrant ................................. 604/28 |
| 5,026,384 | 6/1991 | Farr et al. . |
| 5,053,023 | 10/1991 | Martin ..................................... 604/280 |
| 5,059,179 | 10/1991 | Ya . |
| 5,078,688 | 1/1992 | Lobodzinski et al. .................. 604/164 |
| 5,087,265 | 2/1992 | Summers et al. . |
| 5,135,484 | 8/1992 | Wright . |
| 5,135,531 | 8/1992 | Shiber . |
| 5,163,905 | 11/1992 | Don Michael . |
| 5,163,960 | 11/1992 | Ahmadi . |
| 5,167,239 | 12/1992 | Cohen et al. . |
| 5,184,627 | 2/1993 | de Toledo . |
| 5,192,291 | 3/1993 | Pannek, Jr. . |
| 5,195,955 | 3/1993 | Don Michael . |
| 5,221,256 | 6/1993 | Mahurkar . |
| 5,221,270 | 6/1993 | Parker . |
| 5,250,060 | 10/1993 | Carbo et al. . |
| 5,267,958 | 12/1993 | Buchbinder et al. . |
| 5,279,546 | 1/1994 | Mische et al. . |
| 5,286,253 | 2/1994 | Fucci . |
| 5,318,576 | 6/1994 | Plassche, Jr. et al. . |
| 5,322,508 | 6/1994 | Viere . |
| 5,336,205 | 8/1994 | Zenzen et al. . |
| 5,342,306 | 8/1994 | Don Michael . |
| 5,349,950 | 9/1994 | Ulrich et al. ....................... 128/207.16 |
| 5,370,609 | 12/1994 | Drasler et al. . |
| 5,376,071 | 12/1994 | Henderson ................................. 604/53 |
| 5,376,084 | 12/1994 | Bacich et al. . |
| 5,395,311 | 3/1995 | Andrews . |
| 5,405,322 | 4/1995 | Lennox et al. . |
| 5,415,636 | 5/1995 | Forman . |
| 5,419,774 | 5/1995 | Willard et al. . |
| 5,423,742 | 6/1995 | Theron . |
| 5,431,673 | 7/1995 | Summers et al. . |
| 5,439,000 | 8/1995 | Gunderson et al. . |
| 5,449,343 | 9/1995 | Samson et al. . |
| 5,451,206 | 9/1995 | Young . |
| 5,451,209 | 9/1995 | Ainsworth et al. . |
| 5,460,610 | 10/1995 | Don Michael . |
| 5,462,529 | 10/1995 | Simpson et al. . |
| 5,476,450 | 12/1995 | Ruggio ..................................... 604/93 |
| 5,478,309 | 12/1995 | Sweezer et al. . |
| 5,492,763 | 2/1996 | Barry et al. . |
| 5,496,346 | 3/1996 | Horzewski et al. . |
| 5,500,180 | 3/1996 | Anderson et al. . |
| 5,569,182 | 10/1996 | Twardowski et al. . |
| 5,569,204 | 10/1996 | Cramer ..................................... 604/164 |
| 5,578,018 | 11/1996 | Rowland et al. . |
| 5,634,897 | 6/1997 | Dance et al. . |
| 5,662,671 | 9/1997 | Barbut et al. . |
| 5,695,519 | 12/1997 | Summers et al. . |
| 5,700,252 | 12/1997 | Klingenstein . |
| 5,713,849 | 2/1998 | Bosma et al. ............................ 604/28 |
| 5,743,883 | 4/1998 | Visconti .................................. 604/169 |
| 5,766,211 | 6/1998 | Wood et al. ............................. 604/32 |
| 5,772,642 | 6/1998 | Ciamacco, Jr. et al. . |
| 5,827,229 | 10/1998 | Auth et al. ............................. 604/171 |
| 6,019,350 | 2/2000 | Gelbfish ................................. 251/321 |

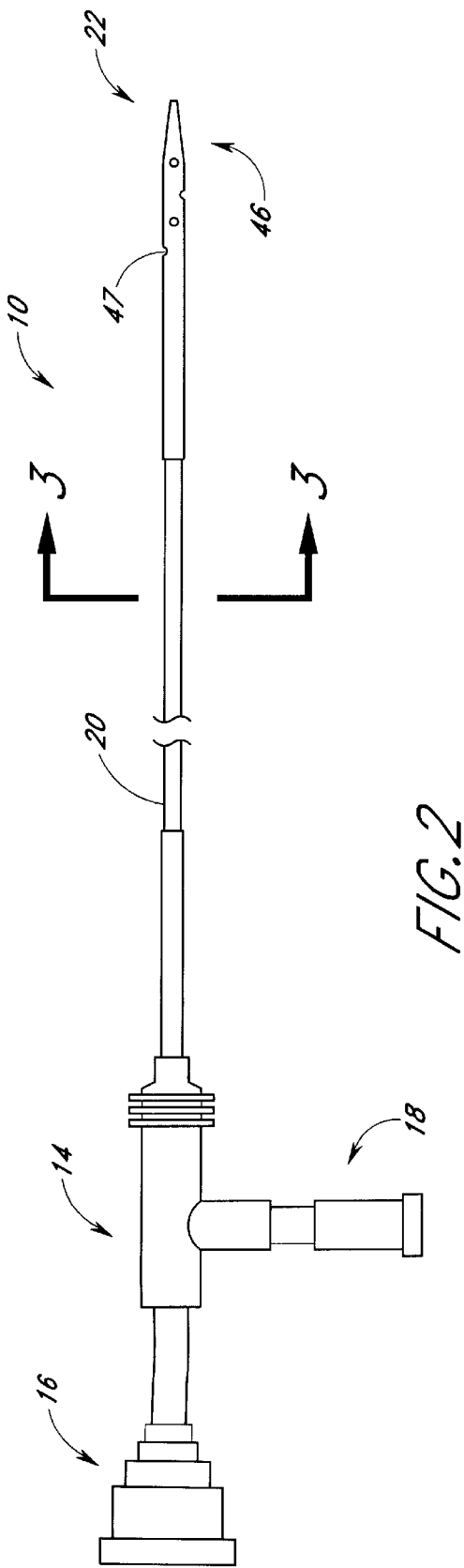
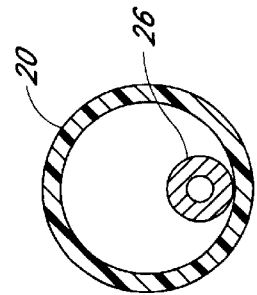
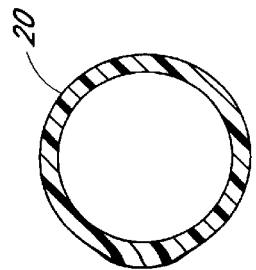

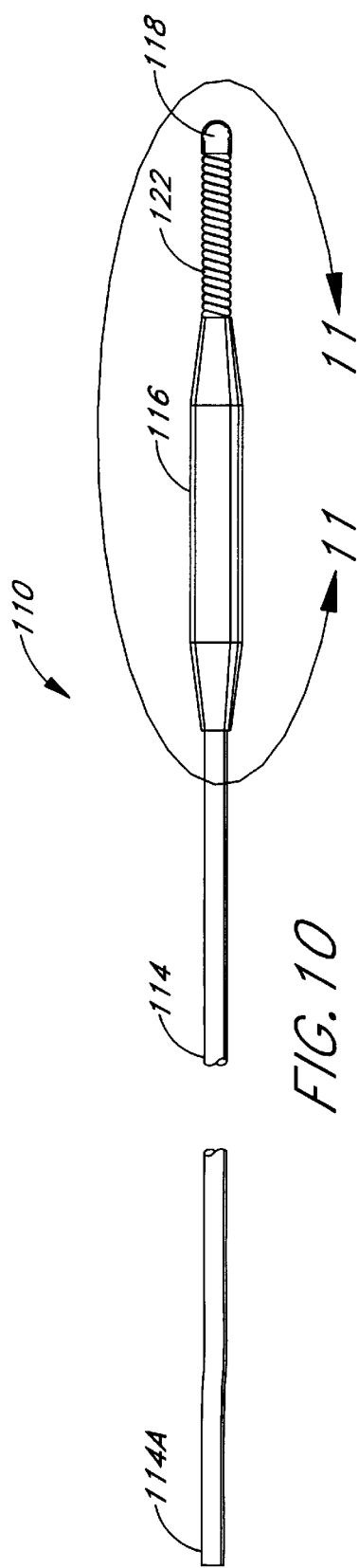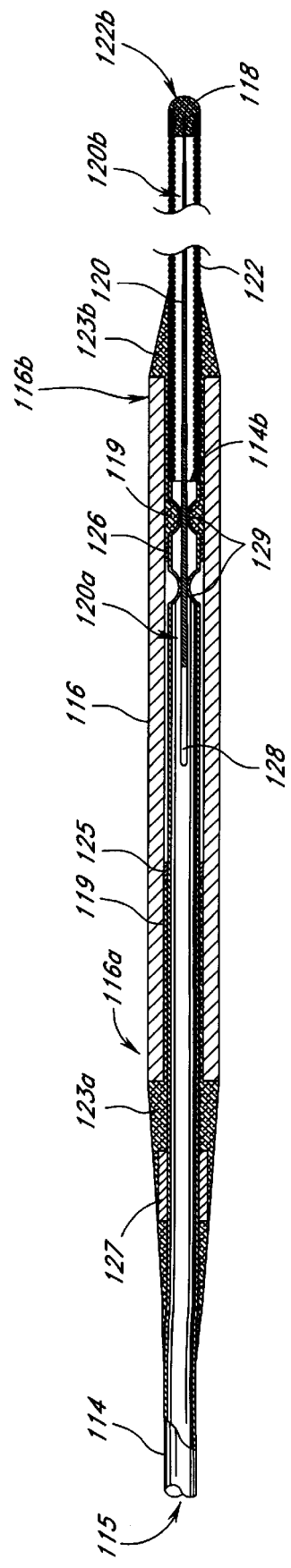

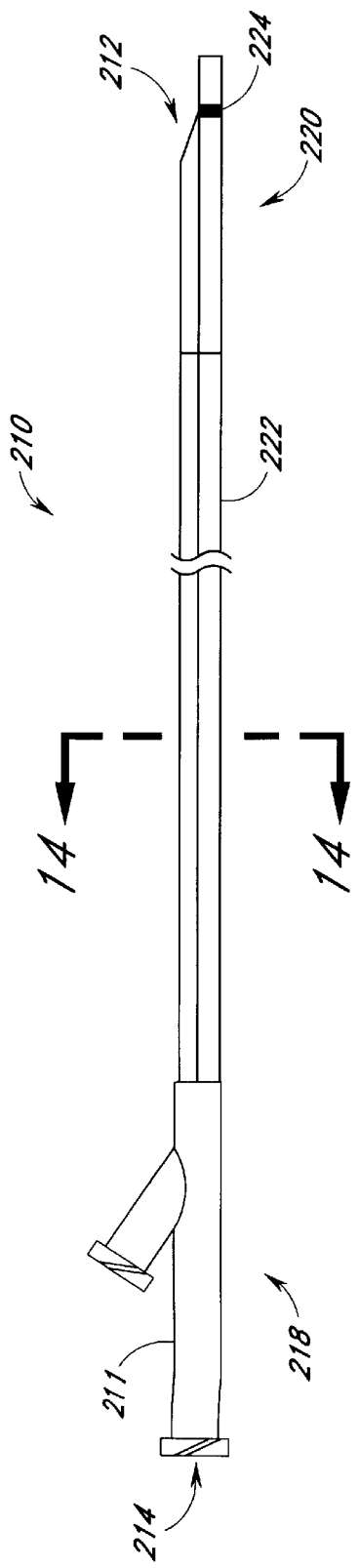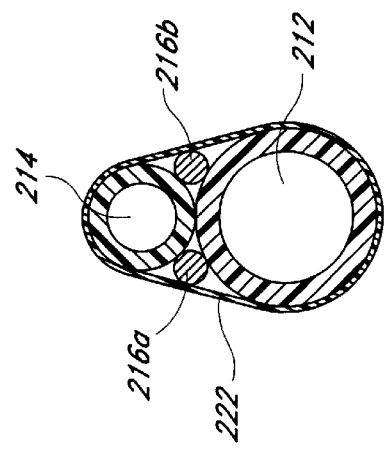

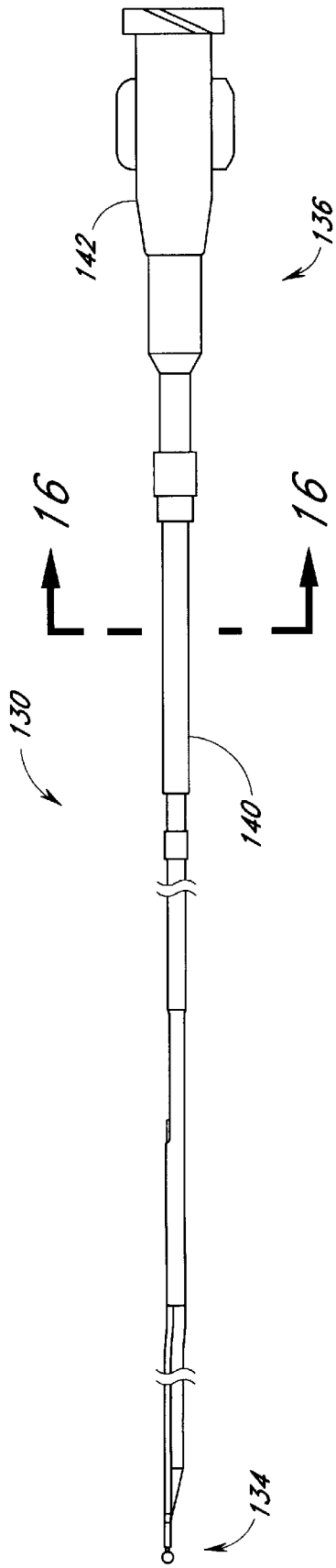
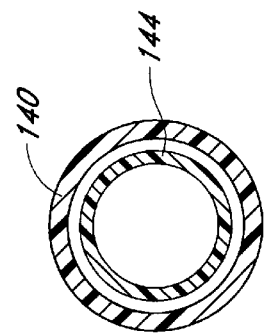
FIG. 15
FIG. 16

ASPIRATION SYSTEM AND METHOD

RELATED APPLICATIONS

This application is a continuation-in-part of U.S. application Ser. No. 08/813,808, filed Mar. 6, 1997 now abandoned, and U.S. application Ser. No. 08/813,807, filed Mar. 6, 1997 now abandoned, and U.S. application Ser. No. 08/812,875, filed Mar. 6, 1997 now U.S. Pat. No. 5,833,644, which is a continuation in part of U.S. application Ser. No. 08/650,464 filed May 20, 1996 now abandoned, all of which are hereby incorporated by reference in their entirety.

BACKGROUND OF THE INVENTION

1. Field of the Invention

The present invention relates to aspiration catheters for aspirating emboli, thrombi, and other types of particles from the vasculature of a patient, the apparatus being particularly well suited for aspiration within saphenous vein grafts, coronary arteries, and similar vessels.

2. Description of the Related Art

Human blood vessels often become occluded or completely blocked by plaque, thrombi, other deposits, emboli or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

Coronary heart disease is an extremely common disorder in developed countries, and is the leading cause of death in the U.S. Damage to or malfunction of the heart is caused by narrowing or blockage of the coronary arteries (atherosclerosis) that supply blood to the heart. The coronary arteries are first narrowed and may eventually be completely blocked by plaque, and may further be complicated by the formation of thrombi (blood clots) on the roughened surfaces of the plaques. Myocardial infarction can result from atherosclerosis, especially from an occlusive or near occlusive thrombi overlying or adjacent to the atherosclerotic plaque, leading to death of portions of the heart muscle. Thrombi and emboli also often result from myocardial infarction, and these clots can block the coronary arteries, or can migrate further downstream, causing additional complications.

Various types of intervention techniques have been developed which facilitate the reduction or removal of the blockage in the blood vessel, allowing increased blood flow through the vessel. One technique for treating stenosis or occlusion of a blood vessel is balloon angioplasty. A balloon catheter is inserted into the narrowed or blocked area, and the balloon is inflated to expand the constricted area. In many cases, near normal blood flow is restored. It can be difficult, however, to treat plaque deposits and thrombi in the coronary arteries, because the coronary arteries are small, which makes accessing them with commonly used catheters difficult.

Other types of intervention include atherectomy, deployment of stents, introduction of specific medication by infusion, and bypass surgery. Each of these methods are not without the risk of embolism caused by the dislodgement of the blocking material which then moves downstream. In addition, the size of the blocked vessel may limit percutaneous access to the vessel.

In coronary bypass surgery, a more costly and invasive form of intervention, a section of a vein, usually the saphenous vein taken from the leg, is used to form a connection between the aorta and the coronary artery distal to the obstruction. Over time, however, the saphenous vein graft may itself become diseased, stenosed, or occluded, similar to the bypassed vessel. Atherosclerotic plaque in saphenous vein grafts tends to be more friable and less fibrocalcific than its counterpart in native coronary arteries.

Diffusely diseased old saphenous vein grafts with friable atherosclerotic lesions and thrombi have therefore been associated with iatrogenic distal embolic debris. Balloon dilatation of saphenous vein grafts is more likely to produce symptomatic embolization than dilatation of the coronary arteries, not only because of the difference in the plaque but also because vein grafts and their atheromatous plaques are generally larger than the coronary arteries to which they are anastomosed. Once the plaque and thrombi are dislodged from the vein, they can move downstream, completely blocking another portion of the coronary artery and causing myocardial infarction. In fact, coronary embolization as a complication of balloon angioplasty of saphenous vein grafts is higher than that in balloon angioplasty of native coronary arteries. Therefore, balloon angioplasty of vein grafts is performed with the realization that involvement by friable atherosclerosis is likely and that atheroembolization represents a significant risk.

Because of these complications and high recurrence rates, old diffusely diseased saphenous vein grafts have been considered contraindications for angioplasty and atherectomy, severely limiting the options for minimally invasive treatment. However, some diffusely diseased or occluded saphenous vein grafts may be associated with acute ischemic syndromes, necessitating some form of intervention.

There is therefore a need for improved methods of treatment for occluded vessels such as saphenous vein grafts and the smaller coronary arteries which decrease the risks to the patient.

SUMMARY OF THE INVENTION

The present invention provides novel aspiration catheters for removing plaque, thrombi, emboli, and other types of obstructions from blood vessels. The present invention advantageously satisfies the need in the prior art by providing a catheter adapted to be compactly utilized in even the smaller size blood vessels. It can also be easily adapted to provide efficient and speedy evacuation in larger size vessels. This system is compatible with more common therapy devices in widespread use today, and is designed for rapid evacuation and ease of use.

The catheters of the present invention are provided in either over-the-wire or in single operator form. The catheters are sized so as to be used in very small blood vessels. Radiopaque markers are preferably incorporated into the distal ends of the catheters to facilitate their positioning within the body; similarly, a marker may be placed on the proximal end of the catheter to aid in the insertion of the catheter in to the patient. The catheters are provided with varying flexibility along the length of the shaft, such that they are soft and flexible enough to be navigated through the vasculature of a patient without causing damage, but are stiff enough to sustain the axial push required to position the catheter properly and to sustain the aspiration pressures. A support mandrel may be incorporated into the catheter to provide additional strength. A support sheath is preferably included to prevent crushing of the aspiration lumen when the catheter is used in conjunction with valves, adaptors or other fittings.

The catheters are preferably sized so as to allow the slidable insertion of a therapy catheter through the main aspiration lumen of the aspiration catheter. Alternatively, the therapy catheter can be built over the aspiration catheter. In either case, the aspiration and therapy catheters can be delivered simultaneously, saving valuable time during the procedure.

One embodiment of the aspiration catheter of the present invention therefore comprises an elongate flexible tubular body having a proximal end and a distal end. The catheter body or shaft incorporates a reinforcement such as a metallic braid or coil or a polymer coil to provide strength and flexibility to the device. A main lumen extends the length of the tubular body, and an aspiration port at the proximal end of the catheter body is in fluid communication with the main lumen, such that aspiration pressure can be provided through the port and main lumen. The distal tip on the catheter is formed of a more flexible material than that used to form the rest of the catheter shaft. Markers are preferably incorporated in to both the distal and proximal ends of the catheter to assist in positioning the catheter in the patient.

The reinforcement can be formed from a variety of materials, including polymers, stainless steel, silver or gold plated stainless steel, ELGILOY, platinum, nitinol, or a combination thereof. The distal end of the catheter body is preferably more flexible than the proximal end, and this can be achieved by providing a braid or coil density at the distal end which is greater than the braid or coil density at the proximal end. At least one support mandrel may be used to provide the catheter with additional strength.

The catheter's main lumen is preferably sized to receive at least one separate catheter, such as a therapy catheter, which is slidably disposed therein. The inner diameter of the main lumen is preferably about 0.045".

The aspiration catheter of the present invention can include a second lumen adjacent the main lumen which is adapted to receive a guidewire therethrough. The second lumen can extend substantially the entire length of the tubular body, or can extend less than 40 cm or less than 20 cm in a proximal direction from the distal end of the body. The second lumen can contain a slit through a side wall to allow insertion and removal of the guidewire therethrough. In a preferred embodiment, the second lumen has an inner diameter of approximately 0.020" to receive a 0.014" diameter guidewire.

The distal tip of the catheter can have at least one side port to facilitate aspiration. The distal tip can be tapered, blunt, or angled to create an oblique opening. The catheter preferably also comprises a valve in fluid communication with the main lumen, to control the application of aspiration pressure at the distal end of the device. The aspiration catheter of the present invention can also incorporate various coatings, such as hydrophilic or hydrophobic coatings, anti-thrombogenic coatings, or a combination thereof.

In another embodiment of the present invention, the aspiration catheter comprises an elongate flexible tubular body having a proximal end and a distal end, a main lumen extending through the tubular body sized to receive at least one separate catheter which is slidably disposed therein, an aspiration port at the proximal end of the tubular body, the aspiration port being in fluid communication with the main lumen, and a tip on the distal end of the tubular body, the tip being formed of a more flexible material than that used to form the tubular body. Again, the catheter can have a second lumen adjacent the first adapted to receive a guidewire therethrough, a specially shaped distal tip, and an optional valve in fluid communication with the main lumen.

In yet another embodiment of the present invention, the aspiration catheter comprises an elongate flexible tubular body having a proximal end and a distal end, a main aspiration lumen through the tubular body, an aspiration port on the proximal end of the tubular body in fluid communication with the main lumen, a therapeutic device attached to the distal end of the tubular body, and a tip on the distal end of the tubular body formed of a more flexible material than that used to form the tubular body itself. The therapeutic device can be an inflatable balloon and the catheter can include a separate inflation lumen for the balloon adjacent the main lumen.

The aspiration catheter may be part of an aspiration system which comprises the aspiration catheter, an extension line having a valve or stopcock to control the delivery of the aspiration pressure, and a source of negative pressure such as a syringe.

Accordingly, the catheters of the present invention provide for very fast and efficient aspiration of the working area surrounding the occlusion in a blood vessel. The catheters can be utilized in a wide range of vessel diameters, including extremely small ones, are easy to use and can quickly and efficiently evacuate occlusions and debris, allowing the physician to restore normal blood flow in these vessels in a very short period of time.

BRIEF DESCRIPTION OF THE DRAWINGS

FIG. 2 is a side view of an over-the-wire aspiration catheter in accordance with the present invention.

FIG. 3 is a cross section of the aspiration catheter of FIG. 2, taken along line 3—3 in FIG. 2.

FIG. 4 is a cross section of the aspiration catheter of FIG. 2 showing a guide wire over which the aspiration catheter rides.

FIG. 10 is a schematic view of an occlusion catheter apparatus for use in the method of the present invention;

FIG. 11 is a schematic cross-sectional view of a distal portion of the catheter apparatus shown in FIG. 10.

FIG. 13 is a side view of another embodiment of the over-the-wire aspiration catheter.

FIG. 14 is a cross-sectional view of the aspiration catheter of FIG. 13, taken along line 14—14 in FIG. 13.

FIG. 15 is a side view of another embodiment of the single operator type aspiration catheter.

FIG. 16 is a cross-sectional view of the aspiration catheter of FIG. 15, taken along line 16—16 in FIG. 15.

DETAILED DESCRIPTION OF THE PREFERRED EMBODIMENTS

The present invention provides novel aspiration catheters for aspirating emboli, plaque, thrombi or other occlusions from a blood vessel and methods of using same. The present invention is adapted for use in the treatment and removal of an occlusion in a blood vessel in which the occlusion has a length and a width or thickness which at least partially occludes the vessel's lumen. Thus, the catheters of the present invention are effective in treating both partial and complete occlusions of the blood vessels. As used herein, "occlusion" includes both partial and complete occlusions, stenoses, emboli, thrombi, plaque and any other substance which at least partially occludes the vessel's lumen.

The method of the present invention can be used to provide aspiration with or without the need for a separate irrigation catheter and irrigation fluid. In the context of removing plaque, thrombi or other blockages from blood vessels, it has heretofore been proposed that an isolated "chamber" surrounding the occlusion be created prior to attempting treatment, and that separate irrigation fluid be provided through an irrigation catheter to the chamber. It has been discovered that isolation of the occlusion is not required in some cases, and that the occlusion can be successfully removed through therapy and/or aspirating of the resulting debris without the need for delivery of a separate irrigation catheter and irrigation fluid in those vessels where certain pressure and fluid flow conditions exist, such as saphenous vein grafts, coronary arteries, carotid arteries and similar vessels.

In non-bifurcated areas of the blood vessels, it has been discovered that fluid from the proximal portion of the same vessel acts as an infusion source. One can therefore occlude only the distal portion of the vessel to create a working area surrounding the occlusion and allow blood to flow from the proximal portion of the vessel into the working area. The working area surrounding the occlusion is aspirated through the guiding catheter or aspiration catheter. It should be noted that, as used herein, "proximal" refers to the portion of the apparatus closest to the end which remains outside the patient's body, and "distal" refers to the portion closest to the end inserted into the patient's body.

Figure 1:
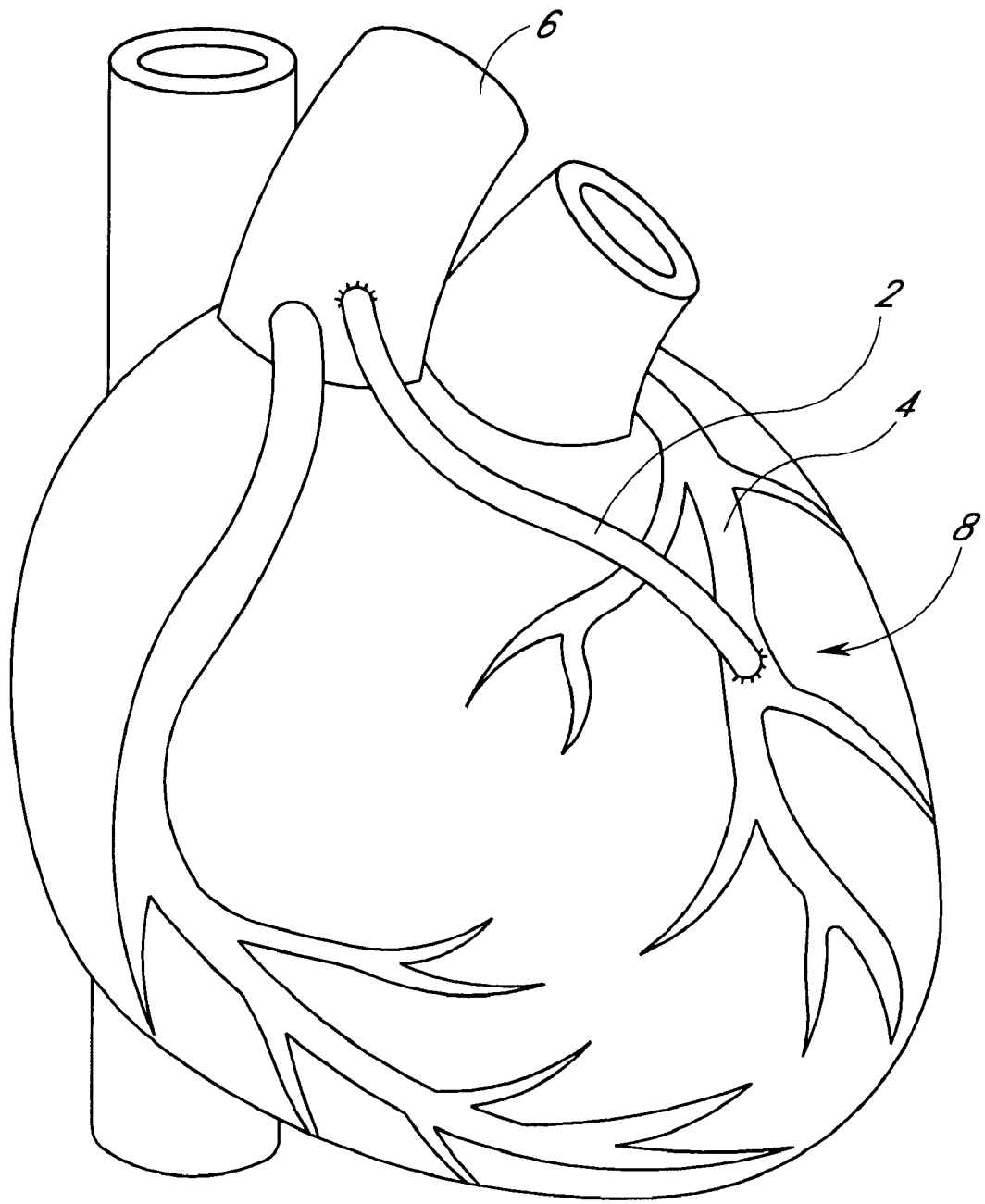
FIG. 1 is a perspective view of a human heart showing a saphenous vein graft used to bypass a portion of the coronary arteries.

The method and apparatus of the present invention can be used in any vessel of the body where the pressure is at least 0.2 psi, and preferably, is about 1.2 psi, with a flow rate of at least 10 cc per minute. The method and apparatus are particularly suited for use in removal of occlusions from saphenous vein grafts, coronary and carotid arteries, and in other non-branching vessels having similar pressures and flow where a suitable working area can be created. A saphenous vein graft is depicted in FIG. 1. The graft 2 is used to bypass one of the occluded coronary arteries 4, and connects the aorta 6 to the coronary artery at a location distal the occlusion 8. Although the present invention will be described in connection with a saphenous vein graft, it should be understood that this application is merely exemplary, and the method can be used in other blood vessels as well.

Apparatus Used With the Present Invention

1. Guide Catheter and Occlusion Catheter

To perform the method of the present invention, a guide catheter having a single lumen is first introduced into the patient's vasculature through an incision made in the femoral artery in the groin and used to guide the insertion of other catheters and devices to the desired site. Following insertion of the guide catheter, a second catheter is inserted through the guide catheter and past the site of the occlusion. The catheter has an occlusive device, such as an inflatable balloon, filter or other mechanical occlusive device, attached at its distal end. The occlusive device should be capable of preventing the migration of particles and debris from the working area, either through total or partial occlusion of the vessel. Note that the occlusion of the vessel need not be complete. Substantial occlusion of the vessel can be sufficient for purposes of the present invention. The catheter should be sized so as to be slidable with respect to the therapy and aspiration catheters inserted over the catheter. The catheter is preferably made of metal such as stainless steel or nitinol, plastics, or composites. A guidewire having an occlusive device on its distal end is also suitable for use in the present method. The method of the present invention can be effectively carried out using a number of guidewires or catheters that perform the function of occluding the vessel and allowing for the slidable insertion of various other catheters and devices. The term "catheter" as used herein is therefore intended to include both guidewires and catheters with these desired characteristics.

A catheter suitable for use in the present invention is illustrated in FIGS. 10 and 11. The catheter apparatus 110 is generally comprised of four communicating members including an elongated tubular member 114, an inflatable balloon member 116, a core-wire member 120 and a coil member 122. The catheter apparatus 110 is preferably provided with an outer coating of a lubricous material, such as Teflon.

The body member 114 of the catheter apparatus 110 is in the form of hypotubing and is provided with proximal and distal ends 114A and 114B as well as an inner lumen 115 extending along the tubular member 114. The balloon member 116 is coaxially mounted near the distal end 114B of the tubular member 114 by suitable adhesives 119 at a proximal end 116A and a distal end 116B of the balloon member 116 as shown in FIG. 11. Proximal and distal tapered portions 123A and 123B on either side of the balloon 116 preferably include adhesives. Proximal and distal adhesive stops 125 and 126 contact the adhesives 119 to define the working length of the balloon 116. A radiopaque marker 127 is preferably located within the proximal tapered portion 123A. A notch 128 in the tubular member 114 permits fluid communication between the lumen 115 and the balloon 116.

A core-wire member 120 of the catheter 110 may be comprised of a flexible wire. The flexible wire 120 is preferably secured to the tubular member 114 within the lumen 115 by a combination of adhesives and crimps 129 (FIG. 11). The proximal end 120A of the flexible wire 120 can have a transverse cross sectional area substantially less than the smallest transverse cross-sectional area of the inner lumen 115 of the tubular member 114. The flexible wire 120 can also taper towards the distal end 120B to smaller diameters to provide greater flexibility to the flexible wire 120. However, the flexible wire 120 may be in the form of a solid rod, ribbon or a helical coil or wire or combinations thereof. As shown in FIG. 11, the distal end 120B of the flexible wire 120 is secured to a rounded plug 118 of solder or braze at the distal end 122B of the coil member 122. The coil member 122 of the catheter 110 may be comprised of a helical coil. The coil member 122 is coaxially disposed about the flexible wire 120, and is secured to the flexible wire 120 by soldering or brazing.

The balloon member 116 is preferably a compliant balloon formed of a suitable elastic material such as a latex or the like. The flexible coil 122 is preferably formed of a wire of platinum or gold based alloys. The flexible core-wire 120 and the tubular member 114 are preferably formed of a superelastic nickel-titanium alloy.

The catheters of the present invention are preferably provided with a coating on the outer surface, or on both the inner and outer surfaces. Suitable coatings include hydrophilic, hydrophobic and antithrombogenic coatings. Examples include heparin, silicone, polyurethane and PVP. These coatings can be applied using methods well known in the art.

Additional details relative to the catheters described above are found in copending U.S. patent applications Ser. Nos. 08/813,023 and 08/812,876, filed Mar. 6, 1997, entitled "Catheter for Emboli Containment System" and "Hollow Medical Wires and Methods of Constructing Same", respectively and U.S. patent applications Ser. Nos. 09/026,225, 09/026,357 and 09/026,105, filed Feb. 19, 1998, entitled "Balloon Catheter and Method of Manufacture", "Core Wire With Shapeable Tip", and "Shaft for Medical Catheters", all of which are hereby incorporated by reference in their entirety.

2. Therapy Catheter

Once the guiding catheter and second catheter have been properly positioned inside the vessel, the occlusive device at the distal end of the catheter is actuated to occlude the vessel distal to the existing occlusion to create a working area. A therapy catheter then is delivered to the site of the occlusion. The term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Various thrombolytic or other types of drugs can be delivered locally in high concentrations to the site of the occlusion. It is also possible to deliver various chemical substances or enzymes via a catheter to the site of the stenosis to dissolve the obstruction. The term "therapy catheter" encompasses these and similar devices.

3. Aspiration Catheter

After the therapy has been performed and the stenosis has been removed or reduced using any of the methods and apparatus described above, the working area is aspirated to remove fluid and debris. Aspiration pressure can be provided through the guide catheter if desired. A source of negative pressure is attached at the proximal end of the guide catheter to create reverse flow, and fluid and debris are aspirated through the guide catheter's main lumen.

Alternatively, an aspiration catheter or similar debris removing device is delivered to the working area to remove particles and any other debris. The term "aspiration catheter" includes any device which creates an area of fluid turbulence and uses negative pressure and reverse flow to aspirate fluid and debris, and includes those devices which create a venturi effect within the vessel. It should be noted that any particles which break free during therapy and aspiration procedures will be kept at the site of the procedure within the working area by the occlusive device occluding the distal portion of the vessel in combination with the blood pressure coming from the proximal portion of the vessel. The debris is prevented from migrating elsewhere, and remains localized for removal by aspiration.

An aspiration catheter particularly suited for use in the treatment and removal of occlusions in blood vessels is illustrated in FIG. 2. The catheter 10 includes an adaptor 14, preferably a female luer adaptor, and a seal 16 at its proximal end. The catheter 10 further includes an aspiration port 18 to which a source of negative pressure is attached. The aspiration catheter further comprises a long tubular body 20 having a distal end 22. The distal tip 22 can include a radiopaque marker to aid in locating the tip 22 during insertion into the patient, and is preferably soft to prevent damage to the patient's vasculature. The aspiration catheter is preferably about 145 cm in length, although this length can be varied as desired.

The aspiration catheter illustrated in FIG. 2 is an over-the-wire catheter. As seen in FIG. 3, the catheter body 20 is hollow, with an internal diameter ranging from about 0.030" to about 0.070". Preferably, the inner diameter is about 0.045". During insertion of the aspiration catheter 10, the proximal end of a guidewire 26 is inserted into the distal end of the aspiration catheter 22, and the aspiration catheter 10 is slidably advanced over the guidewire 26, which is positioned inside the hollow lumen 24 of the aspiration catheter 10. The position of the guidewire 26 relative to the body 20 of the aspiration catheter 10 is illustrated in FIG. 4, but of course can vary. For this type of aspiration catheter 10, a very long guidewire 26, generally around 300 cm in length, is used to facilitate the insertion of the aspiration catheter 10 over the guidewire 26.

Figure 5:
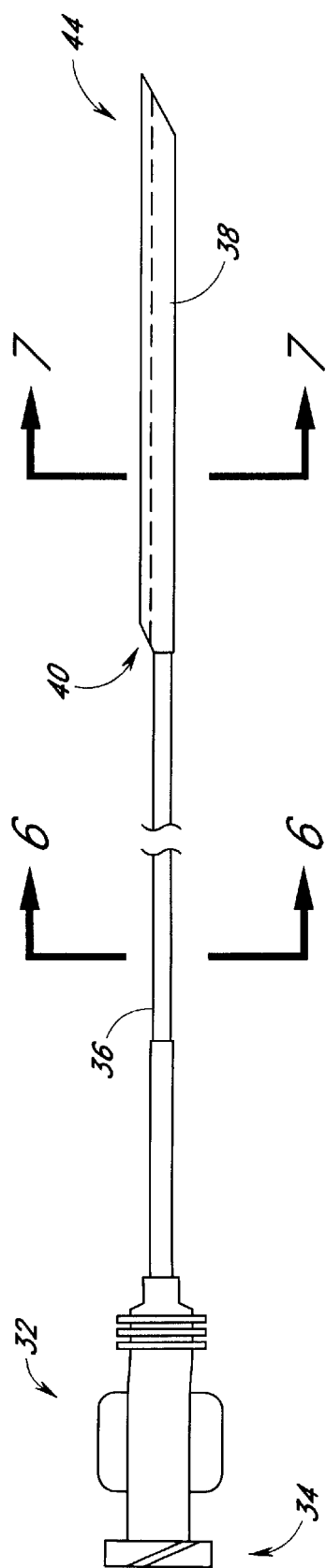
FIG. 5 is a side view of a single operator type aspiration catheter in accordance with the present invention.
Figure 6:
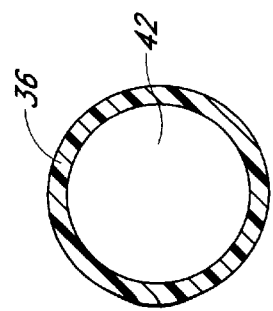
FIG. 6 is a cross section of the proximal end of the aspiration catheter of FIG. 5, taken along line 6—6 of FIG. 5.

Alternatively, the aspiration catheter 30 can be of a single operator design, as illustrated in FIGS. 5–7. The catheter 30 has an adaptor 32 and an aspiration port 34 at its proximal end. Like the over-the-wire aspiration catheter 10, the single operator aspiration catheter 30 further comprises a long tubular body 36 having a distal end 38. The distal tip 38 can include a radiopaque marker to aid in locating the tip 38 during insertion into the patient, and is preferably soft to prevent damage to the patient's vasculature. At the distal end of the shaft 38, a guidewire lumen 40 is attached. This lumen 40 provides a separate lumen, apart from the main aspiration lumen 42 of the catheter 30, for the insertion of the guidewire 26. The inner diameter of the guidewire lumen ranges from about 0.016" to about 0.020" for use with a 0.014" guidewire system. In a preferred embodiment, the inner diameter of the lumen is about 0.019". This guidewire lumen can be less than 10 cm in length, but can extend 30 cm or longer in a proximal direction. As illustrated in FIG. 7, during delivery of the aspiration catheter 30, the proximal end of the guidewire 26 is inserted into the distal end of the guidewire lumen 40, and the guidewire lumen 40 is slidably advanced over the guidewire 26. Unlike the over-the-wire catheter 10 described above, only a short segment of the single operator aspiration catheter 30 rides over the guidewire 26, and the guidewire 26 remains in the guidewire lumen 40 and does not enter the aspiration lumen 42 of the aspiration catheter 30. With the single operator system 30, the long guidewire 26 used with the over-the-wire catheter 10, and the extra operator needed to handle it, are not required.

Figures 7A, 7B:
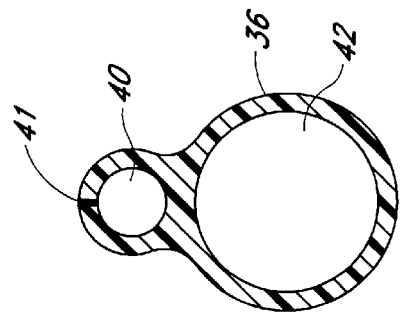
FIG. 7A is a cross section of one embodiment of the distal end of the aspiration catheter of FIG. 5, taken along line 7—7 of FIG. 5.
FIG. 7B is a cross section of another embodiment of the distal end of the aspiration catheter of FIG. 5, also taken along line 7—7 of FIG. 5, showing a slit in the outer wall of the guidewire lumen through which the guidewire can be inserted and removed.

Although the guidewire lumen 40 is shown in FIG. 5 as being located only on the distal end 38 of the shaft of the aspiration catheter 36, the lumen 40 can also be made to extend the entire length of the shaft 36 if desired. In both embodiments, the aspiration lumen 42 is advantageously left completely unobstructed to provide more efficient aspiration. The guidewire lumen 40 can also include a slit 41 along the entire length in the outside wall of the lumen as shown in FIG. 7B to facilitate faster and easier insertion and removal of the guidewire 26 through the side wall of the lumen. By inserting and removing the guidewire through the side wall of the aspiration catheter, the need to remove adapters and attachments from the proximal end prior to slidably advancing or removing the aspiration catheter over the guidewire is eliminated.

In both the over-the-wire and single operator type aspiration catheters, the elongate catheter shaft must have sufficient structural integrity, or "stiffness," to permit the catheter to be pushed through the vasculature to distal arterial locations without buckling or undesirable bending of the body. It is also desirable, however, for the body to be fairly flexible near its distal end, so that the tubular body may be navigated through tortuous blood vessel networks. Thus, in one preferred embodiment, the tubular body of the aspiration catheter is formed from a polymer such as polyethylene or PEBAX (Atochem, France) made to have variable stiffness along its length, with the proximal portion of the tubular body being less flexible than the distal portion of the body. Advantageously, a tubular body of this construction enables a user to more easily insert the tubular body into vascular networks difficult to access using conventional catheters of uniform stiffness. This is because the stiffer proximal portion provides the requisite structural integrity needed to advance the catheter without buckling, while the more flexible distal region is more easily advanced into and through tortuous blood vessel passageways.

In one preferred embodiment, variable stiffness along the length of the catheter shaft is achieved by forming a polymeric tubular body which incorporates a reinforcement along its length. For example, the tubular body may be provided with a reinforcing braid or coil incorporated into its wall structure. The reinforcement can be formed of metal or of various polymers. To achieve variable stiffness, the distal region of the catheter is provided with a braid or coil having a higher braid or coil density than that present in the braid or coil of the proximal region. The lower braid density in the proximal region makes it less flexible, or "stiffer", than the distal region of the catheter.

The precise density of the braiding or coiling provided to the proximal, distal and transition regions can be varied considerably at the time of manufacture, such that catheters having a variety of different flexibility profiles may be created. Moreover, the braid or coil density may be varied within the catheter regions as well, by providing a braid or coil which has a braid or coil density gradient along its length. For example, the most proximal part of the proximal region may be provided with a metallic braid having a braid density of about 50–90 picks per inch, with the braid density increasing at a rate of about 2–5 picks per inch as the braid extends in the distal direction. This reinforced construction of the catheter provides adequate proximal stiffness for axial push, while preventing collapse of the distal tip during aspiration.

A variety of different materials, known to be ductile and shapeable into fine wires, may be used to form the reinforcement. For example, various polymers, stainless steel, silver or gold plated stainless steel, platinum, nitinol, or a combination thereof are suitable. In one preferred embodiment, the braid is formed of stainless steel, and has a braid density which varies from 50–70 picks per inch at the most proximal part of the proximal region of the catheter, to 80–100 picks per inch at the most distal part of the distal region of the catheter.

Reinforcing braids or coils may be introduced into the structure of the catheter body through conventional catheter forming techniques. For example, the tubular body may be formed by inserting a 72D PEBAX tube into a variable braid density stainless steel sleeve, and then inserting the sleeved tube into a 72D PEBAX outer tube of the same length, so that the braided sleeve is sandwiched between the two tubes. A shaping mandrel may be inserted within the inner PEBAX tube, and shaping container over the outer PEBAX tube, and the entire apparatus may then be placed in a hot box kept at a temperature slightly greater than the melting temperature of the PEBAX tubes. The PEBAX tubes will melt and fuse together, and once cooled, will form a tubular body incorporating the braid. This same technique can be used to form a tubular body incorporating a coil.

In another embodiment, variable stiffness of the tubular body may be achieved by forming the proximal and distal regions of the tubular body out of polymeric materials having differing degrees of stiffness. For example, one half of an inner tube of 72D PEBAX may be inserted into an outer tube of 40D PEBAX, and the other half of the inner tube may be inserted into a 72D PEBAX outer tube. The combination may then be heat fused, as described above. The 40D/72D PEBAX combination forms a more flexible tubular body than the region of the 72D/72D PEBAX combination. More or less flexible materials may be used as desired to alter the flexibility of the resulting tubular body. Furthermore, the flexibility of the various regions of a tubular body formed in this manner may be varied further by incorporating a braid or coil having either a uniform braid density or coil pitch, or a varying density or coil, into the tubular body, as described above.

Moreover, any of a variety of different polymeric materials known by those of skill in the art to be suitable for catheter body manufacture may be used to form the catheter body. For example, the body may be formed out of polymers such as polyethylene, PEBAX, polyimide, polyether etherketone, and the like. Different materials might also be combined to select for desirable flexibility properties.

Also, although the catheter body has been described in the context of having two regions of differing flexibility, it will be readily appreciated by those of skill in the art that three or more regions of differing flexibility may easily be provided, by adapting the teachings contained herein.

A further embodiment of the aspiration catheter includes at least one support mandrel incorporated in to the catheter body to further strengthen the catheter. One such catheter having two support mandrels is illustrated in FIG. 13. This over-the-wire aspiration catheter 210 is approximately 135–140 cm. in length, and includes two lumens, an aspiration lumen 212 and a separate guidewire lumen 214. Both lumens 212, 214 extend from the proximal end of the catheter 218 to the distal end 220. As explained above, the catheter 210 preferably includes an adaptor 211 at its proximal end 218. The adaptor 211 connects to a source of negative pressure to provide aspiration through the aspiration lumen 212. During insertion of the aspiration catheter 210, the catheter 210 is slidably advanced over a guidewire positioned within the guidewire lumen 214, as described above.

As illustrated in FIG. 14, the aspiration and guidewire lumens 212, 214 are adjacent one another. Two support mandrels 216a, 216b are positioned alongside the lumens 212, 214 to provide added stiffness to the length of the catheter body 210.

The mandrels 216a, 216b are preferably formed of stainless steel, but could be made of any material which would provide additional strength to the catheter body. The outer diameter of the mandrel is preferably no more the 0.010", to maintain the low profile of the catheter body 210. The mandrels 216a, 216b extend from the proximal end of the catheter body 218, ending approximately 35 cm from the distal end of the catheter 220.

The mandrels 216a, 216b are positioned adjacent the dual lumen tubing 212, 214 of the catheter body 210. A shrink tube 222, formed of polyethylene terephthalate (PET) or other suitable material, surrounds the dual-lumen tubing 212, 214 and the mandrels 216a, 216b. During manufacture of the catheter 210, the shrink tube 222 tightens around the dual lumen tubing 212, 214 and the mandrels 216a, 216b, maintaining the position of the mandrels 216a, 216b adjacent the lumens 212, 214 for the length of the catheter body 210. The shrink tube 222 extends approximately 10 cm past the end of the mandrels 216a, 216b at the proximal end of the catheter 218, to secure the shrink tube 222 around the catheter body 210 and prevent the mandrels 216a, 216b from moving. The shrink tube 222 therefore extends from the proximal end of the catheter 218 to a position approximately 25 cm from the distal tip 220 of the aspiration catheter 210.

The distal tip of the aspiration catheter is preferably formed from 25D to 40D PEBAX with a radiopaque filler such as BaSO4. Alternatively, the distal end of the catheter can also be provided with a soft distal tip which is not pre-formed with the tubular body, but is instead attached to the body as a post manufacturing step. The distal tip is preferably soft enough and flexible enough so as to minimize trauma to body vessels as the catheter is advanced and to facilitate navigation of the catheter in tortuous vessels, but must also be strong enough to avoid collapse during aspiration. In one preferred embodiment, the distal tip is formed as a 0.5 cm sleeve of 25–35D PEBAX and is bonded to the tubular body by use of an adhesive. Alternately, the distal tip may be attached to the tubular body by heat bonding, as is known to those of skill in the art.

The entire distal end of the aspiration catheter can also be attached as a separate post manufacturing step. A tubing made of polyethylene (PE), PEBAX, or polyimide can be fused to the distal end of the main body section of the catheter. This tubing can be from about 5 to about 60 cm in length, but is preferably around 30 cm. The distal end of the aspiration catheter can also be provided with a radiopaque material. Advantageously, radiopaque material serves as a marker 224 to help the user position the catheter inside the patient's body as shown in FIG. 13. Various well-known radiopaque materials may be used in the distal end to form the marker, such as platinum or gold. Alternatively, BaSO4 can be incorporated into the polymer resin itself.

Figure 8A:
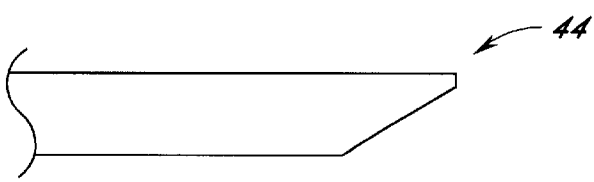
FIGS. 8A–C are side views of the various embodiments of the distal end of the aspiration catheter of the present invention.
Figure 8B:
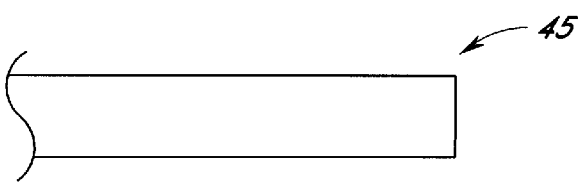
Figure 8C:
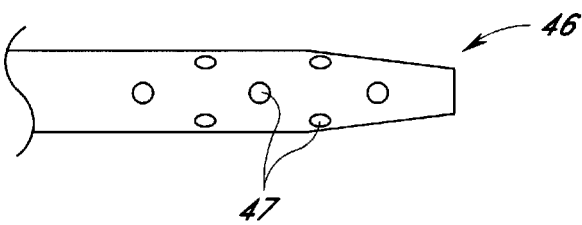

FIGS. 8A, 8B, and 8C illustrate various embodiments of the distal end of the aspiration catheter of the present invention. FIG. 8A shows the preferred tip 44, wherein the end has been angled and is oblique to provide effective retrieval of particles. The angle can be from about 5 degrees to about 90 degrees; an angle of about 25 degrees is preferred. This angled tip 44 is also shown in FIG. 5. This angled tip 44 maximizes the area of aspiration. The distal tip of the aspiration catheter can also be blunt 45, as shown in FIG. 8B, or can be tapered 46. Side ports 47 can be drilled along the distal tip of the catheter to enhance the aspiration rate, as illustrated in FIGS. 8C and 2.

In another embodiment not shown, the aspiration catheter can be configured such that the therapy catheter can be inserted through the lumen of the aspiration catheter. The lumen is made large enough to accommodate the desired therapy catheter. This allows the aspiration catheter and the therapy catheter to be delivered into the patient at the same time. When therapy is complete, the therapy catheter is removed while the aspiration catheter remains in place. This eliminates the need to separately deliver the aspiration catheter after removal of the therapy catheter, saving valuable time. Alternatively, if the shaft of the therapy catheter is sufficiently small to allow aspiration around the catheter, the therapy catheter can remain in place during aspiration. This too saves valuable time by eliminating the need to remove the therapy catheter prior to aspirating. It is preferable that the size of the guide catheter used during this type of procedure be sized from at least 8 to about 10 French to accommodate the size of the "over-the-therapy-catheter" aspiration catheter. Further details regarding aspiration and therapy catheter systems are found in copending application Ser. No. 08/812,570, entitled "Catheter System for Emboli Containment", filed Mar. 6, 1997, which is hereby incorporated by reference in its entirety.

In yet another embodiment, also not shown, the therapy catheter can be built over the aspiration catheter. For example, a dual or triple lumen catheter having a dilatation balloon at its distal end can be used. One lumen is used to inflate the dilatation balloon to be used for angioplasty, while the second lumen is used for aspiration. The third lumen is used as a guidewire lumen. Alternatively, the aspiration catheter can be designed to deploy a stent within the occluded artery, or could include an atherectomy device on its distal end. These designs allows a single combined aspiration catheter and therapy catheter to be delivered into the patient. When therapy is complete, aspiration is carried out without the need to first remove the therapy catheter or separately deliver an aspiration catheter.

Figure 18:
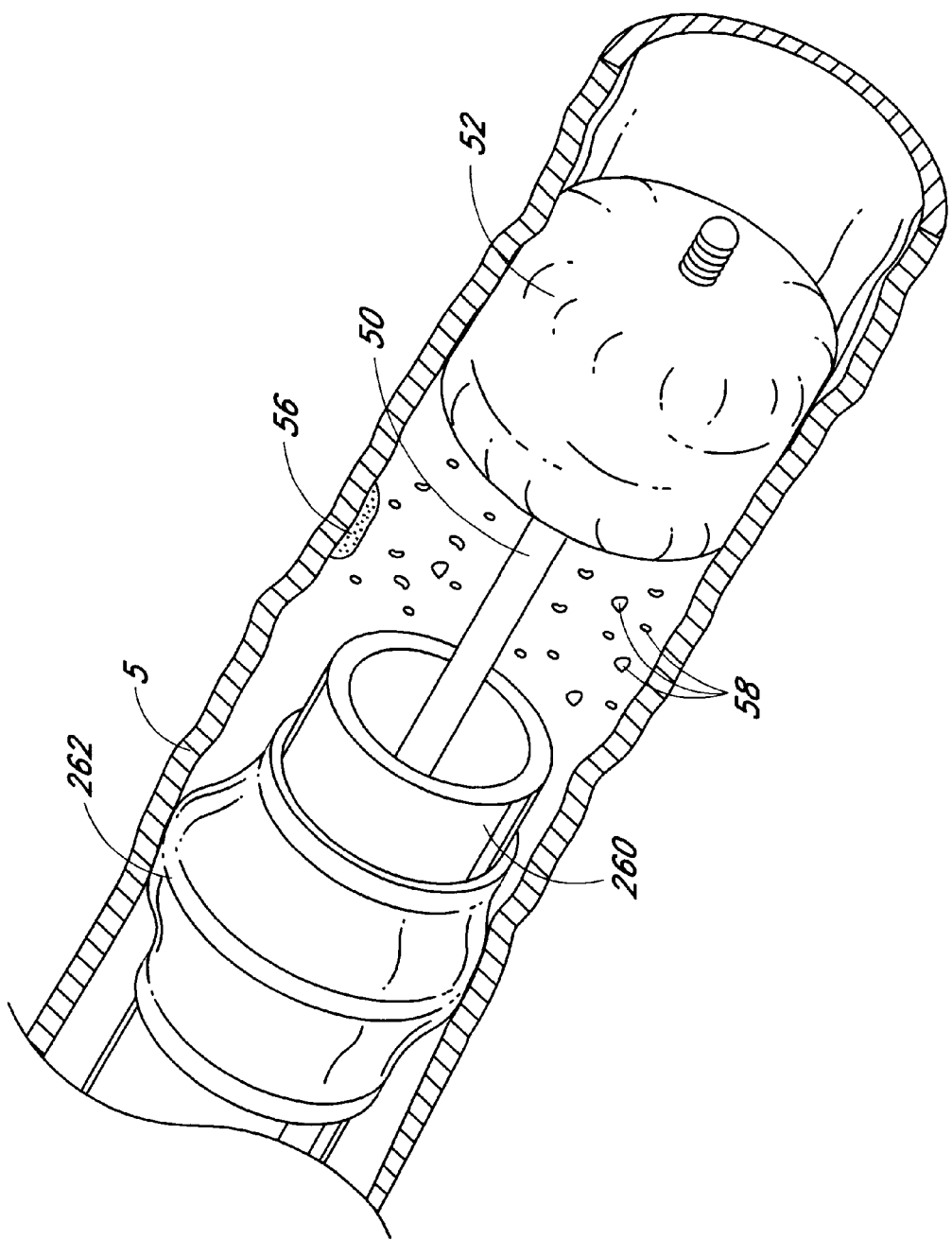
FIG. 18 is a perspective view of an over-the-wire aspiration catheter having an occlusive balloon on its distal end and guidewire inserted into a saphenous vein graft in accordance with the present invention, with the vein graft shown partially cut away.

As illustrated in FIG. 18, the distal end of the aspiration catheter 260 may incorporate an occlusive device 262, such as an inflatable balloon. The balloon 262 is mounted on the distal end of the catheter 260, and an inflation lumen extends the length of the catheter body, from the balloon 262 to the proximal end of the catheter (not shown). As explained below in detail, the aspiration catheter may be used not only for aspiration, but also to occlude the vessel, where desired.

Figure 12:
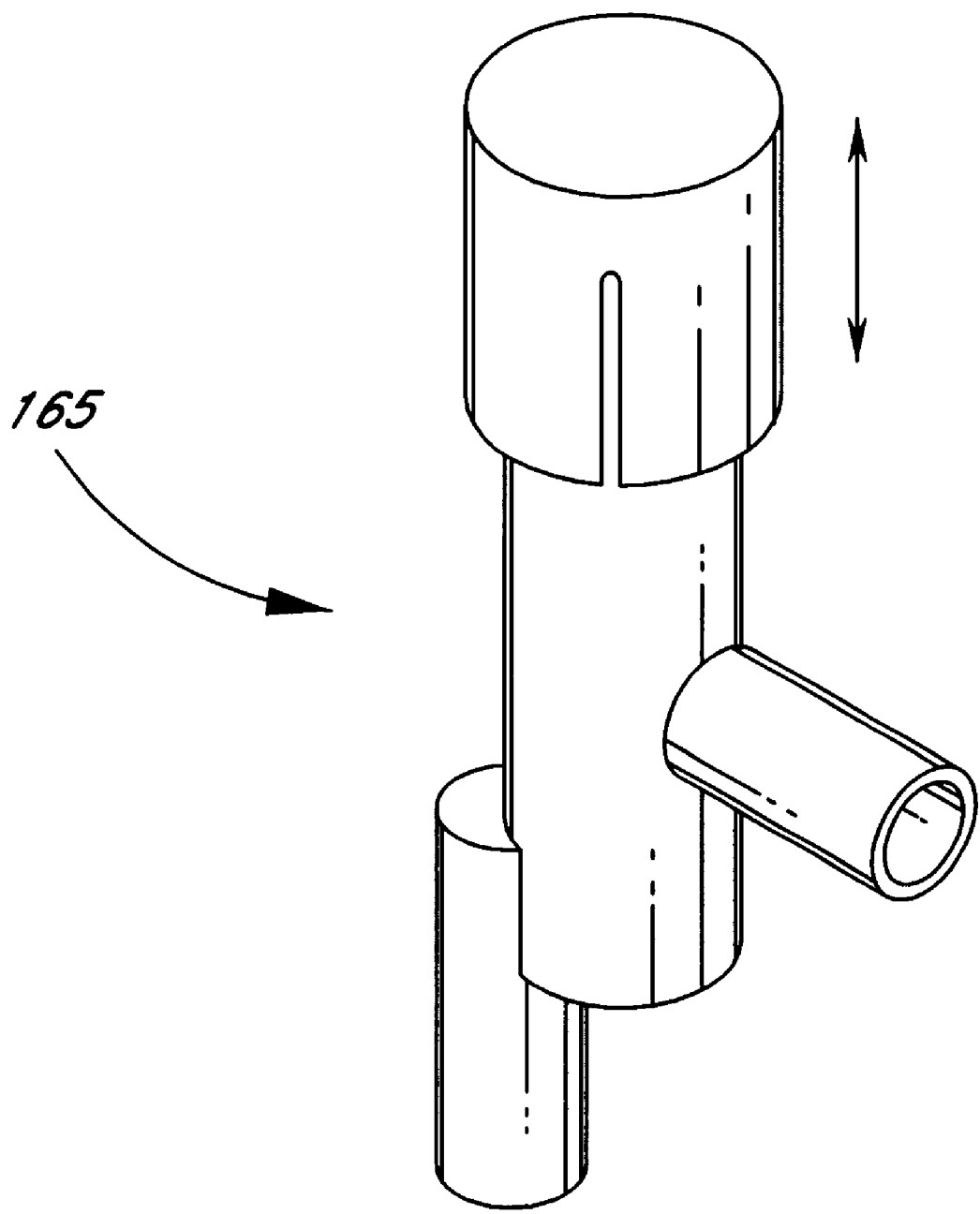
FIG. 12 is a perspective view of a valve which can be positioned at the proximal end of the catheter of the present invention to control aspiration.

The proximal end of the aspiration catheter can be fitted with a valve 165, as illustrated in FIG. 12. The valve 165 allows the user to regulate the aspiration pressure. For example, a syringe can be connected to the valve 165 and aspiration port at the proximal end of the catheter. With the valve 165 closed, the syringe piston can be retracted completely to provide a vacuum. The valve 165 is then opened to provide aspiration at the distal end of the aspiration catheter. Aspiration pressure can be provided in short bursts (pulsed) or continuously as the user desires by opening and closing the valve 165 at the proximal end of the catheter. This valve 165 therefore provides control over the aspiration within the vessel. A preferred valve is available from Burron OEM, a division of B. Braun Medical Inc., under the name TRAC VALVE.

The aspiration catheters of the present invention can also include a coating on the outer surface. Suitable coatings include hydrophilic, hydrophobic, and antithrombogenic coatings, or a combination thereof. Examples of suitable coatings include heparin, silicone, polyurethane and PVP.

The proximal end of the aspiration catheter may also include a marker which indicates to the physician the approximate catheter length which can safely and rapidly be inserted into the patient. This femoral marker is illustrated as part of the aspiration catheter 130 in FIG. 15. This marker 132 is placed on the aspiration catheter 130 approximately 95 cm from the distal tip 134 of the catheter. This length is approximately equal to the distance from the incision site in the femoral artery to the ostium of the coronary artery in the average human being. Thus, during insertion of the catheter 130, the physician rapidly advances the catheter 130 into the patient's vasculature, until the femoral marker 132 near the proximal end of the catheter 136 is just outside the patient's body. At this point, the marker 132 is an indication to the physician to slow the insertion of the catheter 130, and to turn on the fluoroscopy to carefully deliver the distal tip of the catheter 134 to the desired position. This therefore reduces the patient's exposure to x-rays during the procedure. The femoral marker 132 may be made of any biocompatible material, including plastics and metals, however, any visible marker 132 on the outer surface of the catheter 130 may be used.

FIG. 15 illustrates another embodiment of aspiration catheter 130, which incorporates both the femoral marker 132 described above, and a support sheath 140. The support sheath 140 is located on the proximal end of the catheter 136. As described above, the proximal end of the aspiration catheter 136 may include adaptors 142 and valves. For example, commonly used adaptors and valves include a Touhy-Borst or hemostasis valve (not shown), which are positioned at the proximal end of the aspiration catheter 136. The hemostasis valve surrounds the outer surface of the aspiration catheter 130, and tightens down around the aspiration catheter 130 to prevent the patient's blood from flowing out around the aspiration catheter 130. As the valve is tightened, there is some risk that the aspiration catheter 130 may be crushed. Accordingly, a support sheath 140 may be added to the proximal end of the catheter 136 to prevent collapse or crushing of the catheter 136.

In addition, the support sheath 140 allows the aspiration catheter 130 to move within the hemostasis valve. As described below, the physician may wish to move the distal tip of the aspiration catheter 130 in a proximal direction during aspiration, to ensure complete aspiration of debris. If the hemostasis valve is tightened directly onto the aspiration catheter 130, the catheter 130 is not free to slide back and forth. If the valve is tightened on the support sheath 140, however, there is a sufficient gap between the support sheath 140 and the body of the aspiration catheter 130 to allow for slidable movement of the aspiration catheter 130.

The support sheath 140 is preferably about 3–9 cm in length, and more preferably is about 6 cm in length. It is positioned near the proximal end of the catheter 136, just distal to the proximal adaptor 142. The support sheath 140 is preferably formed of polyimide. The sheath 140 surrounds the outer surface of the aspiration catheter 130, as shown in FIG. 16, giving that portion of the aspiration catheter 130 greater strength and preventing the valve from crushing the aspiration lumen 144.

Aspiration System

Figure 17:
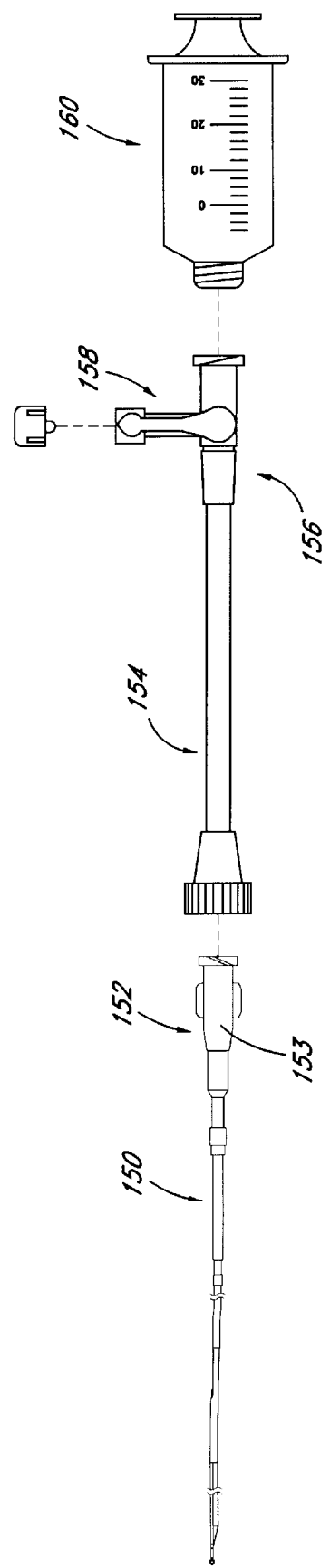
FIG. 17 is a side view of an aspiration system, which includes an aspiration catheter, an extension line having a stopcock, and a source of aspiration pressure.

The aspiration catheter of the present invention may be used as part of an aspiration system, as illustrated in FIG. 17. FIG. 17 illustrates a single operator type aspiration catheter 150; over-the-wire type aspiration catheters may, of course, also be used. The aspiration catheter 150 is connected at its proximal end 152 to an extension line 154, through use of an adaptor 153. Aspiration pressure is provided through the extension line 154 to the aspiration catheter 150. The extension line 154 in turn is fitted with a valve, or stopcock 158, at its proximal end 156. This stopcock 158 controls the delivery of the aspiration pressure through the extension line 154. When the stopcock 158 is in the closed position, no aspiration pressure is delivered to the aspiration catheter 150. It is to be understood that any suitable valve may be used to control the delivery of aspiration pressure to the aspiration catheter. As explained above, use of a valve 158 provides the user with increased control over delivery of the aspiration pressure. A preferred extension line and stopcock assembly is available from Mallinkrodt Medical Inc., Irvine, Calif., catalog no. 140083.

A source of aspiration pressure, such as the syringe 160 illustrated in FIG. 17, is connected to the stopcock 158. If desired, the extension line 154 may be eliminated, and the source of aspiration pressure and the valve 158 may be connected directly to the aspiration catheter 150.

During use, the components of the aspiration system 150, 154, 158 and 160 are assembled as described above. The stopcock 158 or valve is closed, and negative pressure is applied. In the system illustrated in FIG. 17, the plunger on the syringe 160 is retracted to provide negative pressure. To begin aspiration, the stopcock 158 is opened, which supplies negative pressure through the extension line 154 and down to the distal end of the aspiration catheter 150. To stop aspiration, the stopcock 158 is closed. The stopcock 158 may be opened and closed repeatedly to deliver the aspiration pressure in a pulsed manner if desired.

Additional details on various valves and syringe systems are provided in copending applications entitled "Low Profile Catheter Valve and Inflation Adaptor", filed Nov. 20, 1997, Attorney Docket No. PERCUS.006CP1, "Balloon Catheter and Method of Manufacture", Attorney Docket No. PERCUS.010CP1, filed on the same date as the present application, and "Syringe and Method for Inflating Low Volume Catheter Balloons", Attorney Docket No. PERCUS.023CP1, filed on the same date as the present invention, all of which are hereby incorporated by reference in their entirety.

Use of the devices just described will now be explained in connection with the method of the present invention.

Method of the Present Invention

The method of the present invention as used to remove plaque and any associated thrombi from a saphenous vein graft is described below in connection with FIG. 9. Again, it should be noted that this application is merely exemplary, and that the method of the present invention can be used in other blood vessels and to remove other types of occlusions as well.

A guide catheter (not shown) is introduced into the patient's vasculature through an incision in the femoral artery in the groin of the patient. The guide catheter has a single large lumen, and is used to guide the insertion of other catheters and devices. The guide catheter is advanced until it reaches the aorta and the ostium of the vein graft, where it will remain in place throughout the procedure. Fluoroscopy is typically used to guide the guide catheter and other devices to the desired location within the patient. The devices are frequently marked with radiopaque markers to facilitate visualization of the insertion and positioning of the devices within the patient's vasculature.

Next, a catheter or guidewire 50 having an occlusive device at its distal end is delivered through the guide catheter into the saphenous vein graft 5 and past the site of the occlusion 56. In this example, the occlusive device is an inflatable balloon 52. The balloon 52 is inflated to occlude the vein graft 5 at a site distal to the occlusion 56. The blood coming from the aorta enters the saphenous vein graft 5 and keeps any particles 58 dislodged during the procedure from flowing proximally. In addition, the blood pressure and flow coming from the aorta provides the irrigation necessary for aspiration. As noted above, the blood pressure in the vessel is preferably at least about 0.2 psi, and the proximal flow rate is at least about 10 cc per minute.

A therapy catheter (not shown) is then delivered, if desired. The therapy catheter can be any of a number of devices, including a balloon catheter used to perform angioplasty, a catheter which delivers a stent, a catheter for delivering enzymes, chemicals, or drugs to dissolve and treat the occlusion, an atherectomy device, a rheolitic device, or a laser or ultrasound device used to ablate the occlusion. Alternatively, the therapy catheter can be eliminated and use of the guide catheter or a separate aspiration catheter alone can be used to aspirate the occlusion. This method is especially useful to remove emboli from the coronary arteries following acute myocardial infarction, because the aspiration catheter can be made small enough to enter the coronary arteries.

Once the desired therapy is performed, the therapy catheter is withdrawn from the patient's body and an aspiration catheter 60 is delivered over the guidewire 50 and through the guiding catheter. The aspiration catheter 60 rides over the guidewire 50 with the guidewire 50 inserted through the aspiration lumen 62 of the catheter 60. Alternatively, a single operator type aspiration catheter can be used, in which only a portion of the aspiration catheter rides over the guidewire, which is inserted into a separate guidewire lumen. FIG. 9 illustrates the treatment site after the over-the-wire aspiration catheter 60 is inserted into the saphenous vein graft 5.

The distal tip of the aspiration catheter 64 is initially positioned close to the occlusive balloon 52 and aspiration is begun. The operator then slides the aspiration catheter in a proximal direction, increasing the distance between the distal tip 64 and the balloon 52. Aspiration can therefore occur anywhere between about 0 to 20 cm proximal to the occlusive device. If desired, the distal tip of the aspiration catheter 64 can be slidably advanced in the distal direction more than once to ensure complete aspiration of all debris. As explained above, aspiration pressure can be pulsed if desired. Advantageously, the present catheter system and method, which uses a separate aspiration catheter that can be moved back and forth and positioned anywhere within the blood vessels, allows the physician the flexibility to aspirate under a wide variety of conditions and to provide aspiration in a wide variety of locations within the body.

Figure 9:
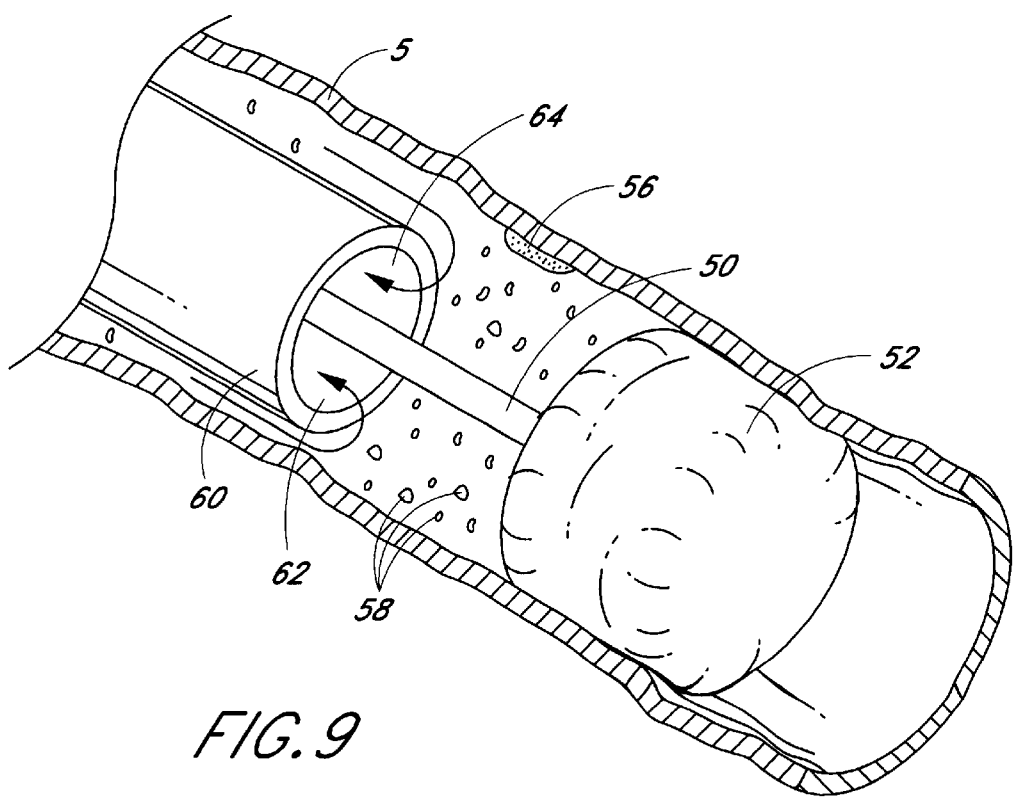
FIG. 9 is a perspective view of an over-the-wire aspiration catheter and guidewire inserted into a saphenous vein graft in accordance with the present invention, with the vein graft shown partially cut away.

The blood pressure supplied by the aorta will move any particles 58 from a position proximal to the distal tip of the aspiration catheter 64, thus allowing them to be aspirated, as illustrated by the arrows in FIG. 9. If a particle, however, is too far distal to the tip of the aspiration catheter 64, the blood pressure will keep it there and not allow it to aspirated from the vessel 5. Once aspiration has begun, additional blood will flow into the area, creating turbulence and allowing for successful removal of debris.

A preferred source of negative pressure is any container containing a fixed vacuum, such as a syringe, attached to the proximal end of the aspiration catheter at the aspiration port 34 (see FIGS. 5 and 17). A mechanical pump or bulb or any other appropriate source of negative pressure can also be used. Other aspiration methods, including those which utilize a venturi effect, can also be used. The difference between the existing pressure within the vessel and the aspiration pressure within the vessel should not exceed 60 psi, and more preferably, should not exceed about 30 psi. If too much aspiration pressure is applied, the change in pressure in the vessel will be too great and damage may occur to the vessel itself.

After the area inside the graft 5 just proximal to the occlusive balloon 52 is aspirated to remove any particles 58 or other debris, the aspiration catheter 60 is removed. The balloon 52 is deflated and the guidewire 50 and guiding catheter are removed.

As described above, the aspiration catheter can be sized such that it can receive the therapy catheter within its lumen, or the therapy catheter can be built over the aspiration catheter. For example, an angioplasty balloon can be attached to the distal end of the aspiration catheter. Alternatively, the aspiration catheter can be designed to deploy a stent within the occluded artery, or could include an atherectomy device on its distal end. The aspiration catheter and the therapy catheter are delivered over the guidewire and into the vein graft together. When therapy is complete, the therapy catheter is removed while the aspiration catheter remains in place. Alternatively, the therapy catheter remains in place during aspiration, eliminating the need to remove the therapy catheter prior to aspiration, which saves precious time. When aspiration is complete, the aspiration catheter, therapy catheter, guidewire and guiding catheter are removed from the patient's body. Delivering the aspiration catheter and therapy catheter together saves time, which is critical during these types of procedures. Alternatively, the guide catheter can be used to provide aspiration through its main lumen.

Alternative Method

An alternate method of the present invention will now be described in connection with FIG. 18. Again, although use of the method in a saphenous vein graft is described, it should be noted that this application is merely exemplary, and that the method of the present invention can be used in other blood vessels and to remove other types of occlusions as well.

As described above, a guide catheter (not shown) is first introduced into the patient's vasculature through an incision in the femoral artery in the groin of the patient. The guide catheter has a single large lumen, and is used to guide the insertion of other catheters and devices. The guide catheter is advanced until it reaches the aorta and the ostium of the vein graft, where it will remain in place throughout the procedure. Fluoroscopy is typically used to guide the guide catheter and other devices to the desired location within the patient. The devices are frequently marked with radiopaque markers to facilitate visualization of the insertion and positioning of the devices within the patient's vasculature.

A guidewire 50 having an occlusive device on its distal end 52 and a catheter having an occlusive device on its distal end, such as the aspiration catheter 260 illustrated in FIG.

18, are delivered to a position just proximal to the occlusion 56. The guidewire 50 and catheter 260 can be delivered together to save time, or can be delivered separately. If delivered together, the guidewire 50 is inserted into the main lumen or guidewire lumen of the catheter 260, and the two are delivered simultaneously. Once the guidewire 50 and catheter 260 are in position proximal to the occlusion 56, the occlusion balloon 262 on the end of the catheter 260 is inflated, occluding the vessel 5. The guidewire 50 is then advanced across the occlusion 56, until the occlusion balloon 52 is distal to the occlusion 56. The occlusion balloon 52 on the guidewire 50 is then inflated. This method is particularly useful in saphenous vein grafts 5 where the occlusion 56 tends to be friable, and there is a greater risk of dislodging particles 58 which could then travel downstream.

The occlusion balloon 262 proximal to the occlusion is then deflated. The aspiration catheter 260 is then used to aspirate any loose particles 58 from the area proximal to the occlusion balloon 52 positioned distal to the occlusion 56. Alternatively, if an aspiration catheter is not used to occlude the vessel, the catheter bearing the proximal occlusive device is removed following deactivation of the occlusive device, and a separate aspiration catheter is delivered and used to aspirate the area proximal to the distal occlusion balloon 52.

The aspiration catheter 260 is then removed. The occlusion balloon 52 on the guidewire 50 remains inflated, occluding the vessel 5 at a site distal to the occlusion 56. As described above, therapy is then performed on the occlusion, the area is aspirated, the distal occlusion balloon 52 is deflated, and the guidewire 50 and guiding catheter are removed.

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

What is claimed is:

1. A catheter system, comprising:
    an aspiration catheter having a proximal end, a distal end, a hollow aspiration lumen, and a hollow guidewire lumen sized and configured to receive a guidewire therethrough, wherein the aspiration lumen and guidewire lumen are adjacent one another;
    a valve in fluid communication with the aspiration lumen of the aspiration catheter;
    a hollow extension line in fluid communication with the aspiration lumen and the valve;
    a source of negative pressure in fluid communication with the aspiration lumnen and the valve;
    one or more support mandrels positioned alongside the aspiration lumen and guidewire lumen; and
    a shrink tube that surrounds at least a portion of the aspiration lumen, guidewire lumen, and one or more support mandrels.

2. The catheter system of claim 1, wherein the shrink tube is formed of polyethylene terephthalate (PET).

* * * * *

UNITED STATES PATENT AND TRADEMARK OFFICE
CERTIFICATE OF CORRECTION

| | |
|---|---|
| PATENT NO. | : 6,152,909 |
| DATED | : November 28, 2000 |
| INVENTOR(S) | : Celso J. Bagaoisan and Hung V. Ha |

It is certified that error appears in the above-identified patent and that said Letters Patent is hereby corrected as shown below:

A Petition to Correct Inventorship Under 37 C.F.R. § 1.48(b) was filed with the United States Patent and Trademark Office on May 25, 2000, deleting as inventors Mukund R. Patel, Sivette Lam and Mir Imran.

Signed and Sealed this

Second Day of October, 2001

*Attest:*

*Attesting Officer*

NICHOLAS P. GODICI
*Acting Director of the United States Patent and Trademark Office*